(12) United States Patent
Greiner-Perth

(10) Patent No.: US 9,352,345 B2
(45) Date of Patent: May 31, 2016

(54) DISPENSER HEAD FOR A CONTAINER AND METHOD FOR FASTENING A DISPENSER HEAD TO A CONTAINER

(71) Applicant: Juergen Greiner-Perth, Gottmadingen (DE)

(72) Inventor: Juergen Greiner-Perth, Gottmadingen (DE)

(73) Assignee: APTAR RADOLFZELL GMBH, Radolfzell (DE)

( * ) Notice: Subject to any disclaimer, the term of this patent is extended or adjusted under 35 U.S.C. 154(b) by 0 days.

(21) Appl. No.: 14/260,657

(22) Filed: Apr. 24, 2014

(65) Prior Publication Data

US 2014/0319185 A1    Oct. 30, 2014

(30) Foreign Application Priority Data

Apr. 26, 2013   (EP) .................................... 13165629

(51) Int. Cl.
| | | |
|---|---|---|
| *B05B 11/00* | (2006.01) | |
| *A61M 15/00* | (2006.01) | |
| *A61M 15/08* | (2006.01) | |
| *B65D 83/22* | (2006.01) | |

(52) U.S. Cl.
CPC .......... *B05B 11/0008* (2013.01); *A61M 15/009* (2013.01); *A61M 15/08* (2013.01); *A61M 2207/00* (2013.01); *B05B 11/3047* (2013.01); *B05B 11/3059* (2013.01); *B65D 83/228* (2013.01); *Y10T 29/49826* (2015.01)

(58) Field of Classification Search
CPC ............ B05B 11/0008; B05B 11/3047; B05B 11/3059; A61M 15/009; A61M 15/08; A61M 2207/00; Y10T 29/49826; B65D 83/228
USPC ................ 222/153.14, 321.6, 321.9
See application file for complete search history.

(56) References Cited

U.S. PATENT DOCUMENTS

| | | | |
|---|---|---|---|
| 3,367,540 A | | 2/1968 | Lehmann |
| 3,403,823 A | | 10/1968 | O'Donnell |
| 4,624,393 A | * | 11/1986 | Lopez ....................... A61J 1/06 222/83.5 |
| 5,941,428 A | * | 8/1999 | Behar ................. B05B 11/3049 222/321.7 |
| 6,439,440 B1 | * | 8/2002 | Lasserre .................. 222/402.21 |

FOREIGN PATENT DOCUMENTS

| | | |
|---|---|---|
| DE | 1 475 179 A1 | 1/1969 |
| EP | 2 388 075 A1 | 11/2011 |
| FR | 2 527 562 A1 | 12/1983 |
| FR | 2 635 085 A1 | 9/1990 |
| FR | 2 946 962 A1 | 12/2010 |
| GB | 1 109 829 A | 4/1968 |

OTHER PUBLICATIONS

European Patent Office Search Report issued in European Application No. 13 16 5629 with English translation of category of cited documents dated Sep. 11, 2013 (8 pages).

* cited by examiner

*Primary Examiner* — Nicholas J Weiss
(74) *Attorney, Agent, or Firm* — Flynn, Thiel, Boutell & Tanis, P.C.

(57) ABSTRACT

A dispenser head for dispensing a liquid or pasty medium, which dispenser head is fastenable to a container storing the medium, including an intermediate element with a receiving opening for the container and an actuating handle which is coupled displaceably in an actuating direction to the intermediate element, wherein the intermediate element and/or the actuating handle have/has at least one releasable connecting element providing a retaining force between the intermediate element and the actuating handle, which retaining force is opposed to a relative movement between the intermediate element and the actuating handle.

9 Claims, 2 Drawing Sheets

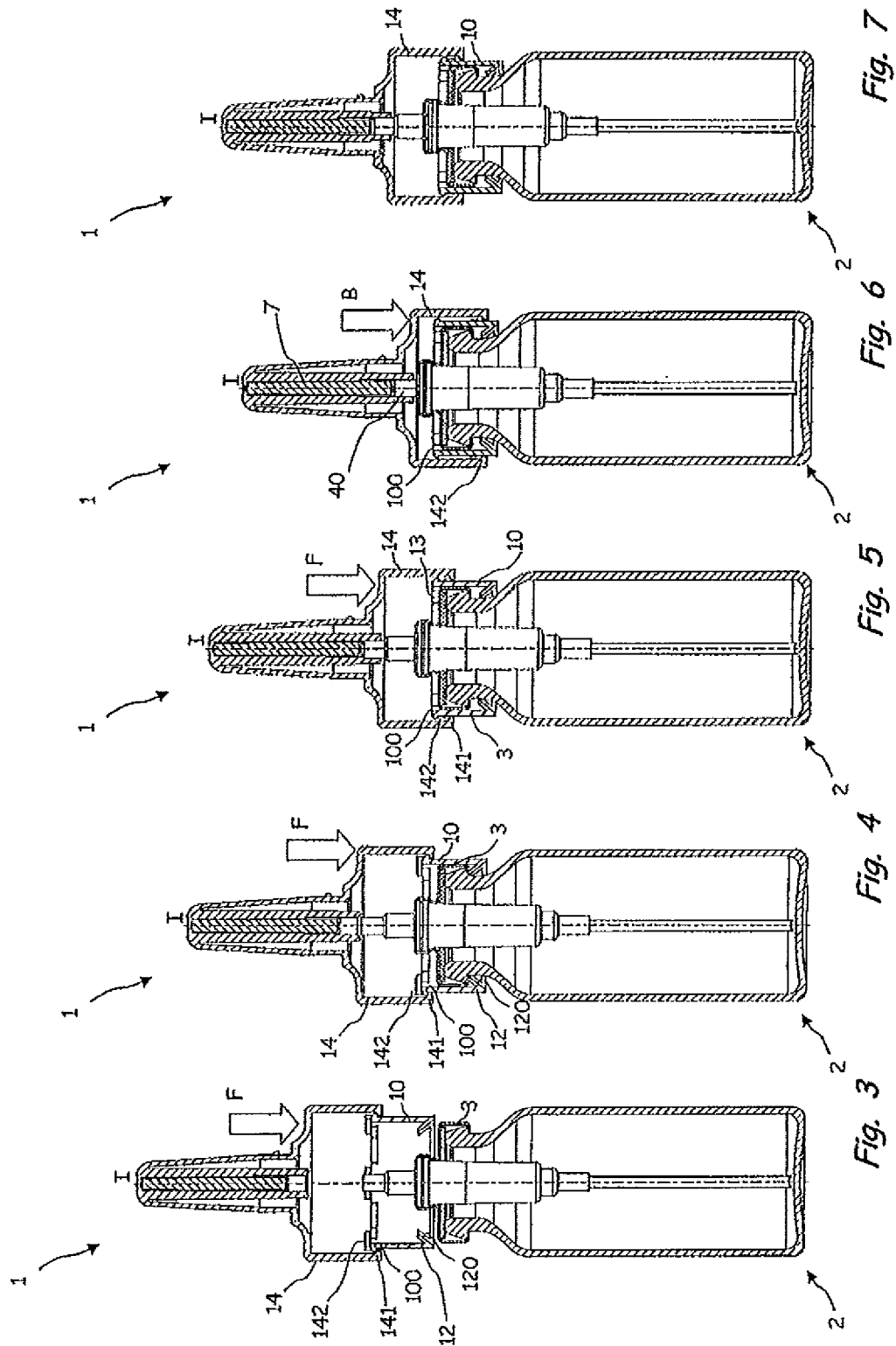

DISPENSER HEAD FOR A CONTAINER AND METHOD FOR FASTENING A DISPENSER HEAD TO A CONTAINER

CROSS-REFERENCE TO RELATED APPLICATION

This application claims priority from European Patent Application No. 13165629.0 filed on Apr. 26, 2013, the disclosure of which is hereby incorporated by reference in its entirety into this application.

FIELD OF THE INVENTION

The invention relates to a dispenser head for dispensing a liquid or pasty medium which is fastenable to a container storing the medium, comprising an intermediate element with a receiving opening for the container and an actuating handle which is coupled displaceably in the axial direction of the intermediate element to the intermediate element. The invention furthermore relates to a dispenser comprising a dispenser head and a container, and to a method for fastening a dispenser head to a container.

The intermediate element is connected to the container. The actuating handle is moveable relative to the intermediate element and therefore relative to the container in order to discharge a medium.

BACKGROUND OF THE INVENTION

Dispenser heads of this type are useable both for cosmetic products and for medicaments. The dispenser head is customarily attached to the container by a filler after the container has been filled. Various fastening methods, such as screwing, adhesive bonding or the like, are known therefor.

If the container stores a medicament, it is desirable that a connection between the container and the dispenser head is possible only by application of high forces and/or, for example for child protection, only by complex movement patterns. It is therefore known to provide a latching geometry on the container and/or the dispenser head, wherein the dispenser head is snapped and/or pushed onto the container. In conjunction with the application, production of a latching connection by forces applied in a pulsed manner is referred to here as pushing. In contrast thereto, snapping-on takes place by a relative movement of the components to be connected, wherein assembly forces act over a prolonged period which is dependent on the particular assembly operation.

It is known from EP 2 388 075 A1 to push a spray head onto a container. A protective cap is arranged here over the spray head, wherein forces are applied for pushing the protective cap on and are transmitted to the fastening geometry by means of the protective cap. By means of a such a protective cap, it is intended to be possible to push the spray head onto the container without otherwise loading the pump.

SUMMARY OF THE INVENTION

It is the object of the invention to provide a dispenser head which is fastenable securely and simply to a container. It is a further object of the invention to provide a method for the secure and simple fastening of a dispenser head to a container.

According to a first aspect of the invention, a dispenser head for dispensing a liquid or pasty medium is provided, which dispenser head is fastenable to a container storing the medium and which comprises an intermediate element with a receiving opening for the container and an actuating handle coupled displaceably to the intermediate element, wherein the intermediate element and/or the actuating handle have/has at least one releasable connecting element providing a retaining force between the intermediate element and the actuating handle, which retaining force is opposed to a relative movement between the intermediate element and the actuating handle in the actuating direction.

The intermediate element is connected to the container during the assembly. In one refinement, the "intermediate element" is a substantially tubular component which is also referred to as a sleeve. However, in conjunction with the application, the design of the intermediate element is not limited to the design as a sleeve. The intermediate element can have a geometry which is suitably selectable by a person skilled in the art and permits a displaceable coupling to the actuating handle.

Filling of the container and attaching of the dispenser head to the container customarily take place at a filler. By means of the connecting element, fixing of the actuating handle, which is coupled displaceably to the intermediate element during use, is possible in a delivery state at the filler. As a result, an undefined position between the actuating handle and the intermediate element, which position makes assembly of the dispenser head difficult, is avoided. The connecting element is releasable during or after assembly.

After the dispenser head is assembled to the container, a relative movability between the intermediate element and the actuating handle, which is coupled displaceably to the intermediate element, and consequently also between the actuating handle and the container, to which the intermediate element is fastened, is useable in order to bring about a discharge of the medium stored in the container. For this purpose, in one refinement, the actuating handle has suitable engagement surfaces, such as finger rests or the like. In other refinements, for a discharge of the medium, a force is applied to the container, said force being used to bring about a relative movement between the container and the actuating handle.

In one refinement, the medium is stored under pressure in the container, wherein the relative movement opens a valve for a discharge. In another refinement, a pump device is provided, said pump device being actuated by the relative movement between the actuating handle and the container. In one refinement, the pump device is prefitted here to the container before an assembly of the dispenser head.

In one refinement, the actuating handle also serves as a housing for the dispenser head which, after the assembly, for example, houses pump device elements protruding from the container. Alternatively or in addition, in other refinements, the elements of the pump device are housed in the intermediate element.

In advantageous refinements, the actuating handle has a discharge opening which is connected by means of a discharge channel to an outlet opening of the container and/or to a pump device arranged in the container. In other refinements, a discharge opening is provided on the intermediate element.

In one refinement, the at least one connecting element is designed in such a manner that said connecting element is destroyed during assembly and, after assembly, is thereby not opposed to a relative movement between the intermediate element and the actuating handle.

In other refinements, the at least one connecting element is unlocked or released, wherein, after release of the at least one connecting element, the intermediate element and the actuating handle are coupled displaceably to each other within a displacement distance. In order to prevent the released connecting element from interfering with a relative movement for discharge purposes, in advantageous refinements, the connecting element is arranged outside the displacement distance. In conjunction with the application, the reversing points are referred to as upper and lower dead centre, wherein, in order to reach the upper dead centre, the components are at a maximum distance apart and, when the lower dead centre is reached, the components are pushed one inside the other to the maximum extent. The connecting element is preferably located in a region behind the upper dead centre, and therefore, during the assembly, the components are arranged away from each other via the region of the displacement distance.

The dispenser head is fastened to the container. In one refinement, fastening takes place by means of a frictional connection. The dispenser head, or more precisely a receiving opening of the intermediate element, and the container have a suitable geometry, depending on requirements, for the screwing, adhesive bonding or the like of the components. In advantageous refinements, fastening takes place in a substantially axially fixed manner, wherein, depending on requirements, play remains between the intermediate element and the container.

In an advantageous refinement, it is provided that the receiving opening has a latching geometry for the fastening to the container. In one refinement, the latching geometry comprises a latching hook which engages behind a latching projection, a latching groove, a latching undercut or the like on a counterpart. In advantageous configurations, the receiving opening has a latching hook. However, configurations are also conceivable in which a latching hook is provided on the container. In advantageous refinements, the latching geometry is designed in such a manner that the intermediate element is snappable and/or pushable onto the container by movement in the actuating direction. In one refinement, for the snapping-on and/or pushing-on operation, a force is applied to the intermediate element. In advantageous refinements, it is provided that a force to be applied for snapping and/or pushing the intermediate element onto the container is smaller in the actuating direction than the retaining force, which is applied by the at least one connecting element, between the intermediate element and the actuating handle in the actuating direction. The intermediate element and the actuating handle are fixable here in the fixed state to the container, wherein a force is introduced via the actuating handle. As described above, the connecting element is preferably located in a region behind the upper dead centre, and therefore the components are arranged away from each other over the region of the displacement distance during the assembly. As a result, a collision of the actuating handle with elements of a pump unit at the beginning of assembly is prevented.

In a further refinement, a stop is provided on the receiving opening, said stop being used to limit a movement of the intermediate element relative to the container during the snapping-on and/or pushing-on operation. A distance between the at least one stop and a contact surface of the latching geometry therefore determines a fastening region for the container. After the snapping-on and/or pushing-on operation, the intermediate element is connected to the container with play and/or in a clamping manner, depending on the height of the fastening region.

According to a second aspect, a dispenser for a liquid or pasty medium is provided, with a container storing the medium and a dispenser head, which is fastened to the container, comprising an intermediate element with a receiving opening for the container and an actuating handle which is coupled displaceably in an actuating direction to the intermediate element, wherein the intermediate element and/or the actuating handle have/has at least one releasable connecting element providing a retaining force between the intermediate element and the actuating handle, which retaining force is opposed to a relative movement between the intermediate element and the actuating handle in the actuating direction.

The container has a fastening geometry which is complementary to the receiving opening. In one refinement, a crimped sleeve is arranged on an opening of the container. The container is securely closed by means of the crimped sleeve. In advantageous refinements, the crimped sleeve also supports a valve and/or a pump unit for the discharge of the medium. In advantageous refinements, the crimped sleeve is designed in such a manner that it has at least two planar surfaces, on which a latching geometry and a stop of the receiving opening engage.

According to a third aspect, a method for fastening a dispenser head, for the discharge of a liquid and pasty medium, to a container storing the medium is provided, wherein the dispenser head comprises an intermediate element with a receiving opening for the container and an actuating handle which is coupled displaceably in an actuating direction to the intermediate element, characterized in that, during the fastening of the intermediate element to the container, a relative movement between the intermediate element and the actuating handle in the actuating direction is blocked by at least one connecting element providing a retaining force in the actuating direction, and, after the intermediate element is fastened to the container, the at least one connecting element is released.

Owing to the fixing, an undefined position between the intermediate element and the actuating device is prevented. The fixing here preferably takes place in such a manner that the intermediate element and the actuating device are not arranged in a lower dead centre of the displacement distance. The intermediate element and the actuating device are preferably displaced relative to each other beyond an upper dead centre of a displacement distance, which is provided during use, and fixed. In one refinement, it is provided that the intermediate element is snappable and/or pushable onto the container by movement in the actuating direction. For this purpose, the receiving opening and/or the container have a latching geometry. By suitable design of the latching geometry and the at least one connecting element, provision is made here for the intermediate element to be snapped and/or pushed onto the container before a force acts on the at least one connecting element, which force exceeds the retaining force, which is applied by the at least one connecting element, between the intermediate element and the actuating handle in the actuating direction. As a result, it is ensured that, during the assembly, the actuating handle remains fixed to the intermediate element by movement in the actuating direction.

In a further refinement, it is provided that a movement of the intermediate element relative to the container during the snapping-on and/or pushing-on operation is limited by at least one stop arranged on the receiving opening, wherein, by a further movement of the actuating handle in the actuating direction, a force exceeding the retaining force is applied to the at least one connecting element in the actuating direction, and therefore the at least one connecting element releases. As described above, the intermediate element and the actuating device are preferably displaced relative to each other beyond an upper dead centre of a displacement distance, which is provided during use, and fixed. The stop is preferably positioned in such a manner that, when the stop is reached, with the exception of the fastening geometry there is still no contact between the components of the dispenser head and the components of the container. After the dispenser head is fixed to the container, an inadvertent discharge of the medium is therefore still prevented. Only by application of a further assembly force is a release of the connecting element brought about, wherein the components of the dispenser head, such as a discharge channel, and of the container, in particular a pump unit, are also connected to each other.

In a further refinement, it is provided that a valve unit and/or a pump unit is prefitted on an opening of the container by means of a crimped sleeve.

BRIEF DESCRIPTION OF THE DRAWINGS

Further aspects and advantages of the invention are also apparent from the description below of preferred exemplary embodiments of the invention and the drawings in which:

FIGS. 3 to 5 show schematically an assembly of the dispenser head 1 according to FIG. 1 on a container 2 according to FIG. 2; and FIGS. 6 and 7 show schematically an actuation of the fitted dispenser head 1 according to FIG. 1 for the dispensing of a medium.

DETAILED DESCRIPTION OF AN EXEMPLARY EMBODIMENT

Figure 1:
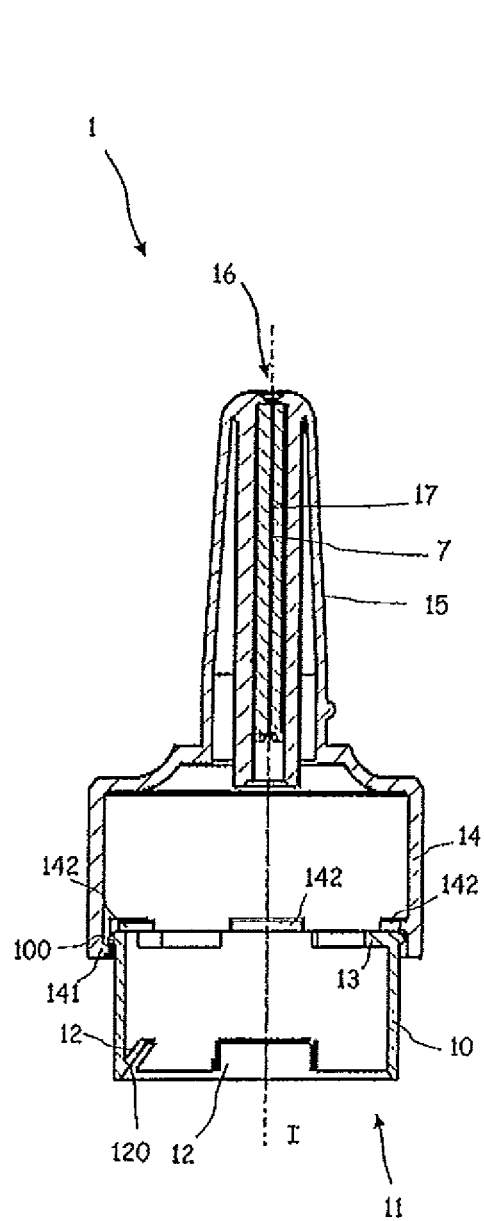
FIG. 1 shows schematically a dispenser head 1 for a dispenser.

FIG. 1 shows schematically a dispenser head 1 for a dispenser for dispensing liquid or pasty media. The dispenser head is fastenable, for example, to a container 2, as illustrated in FIG. 2.

Figure 2:
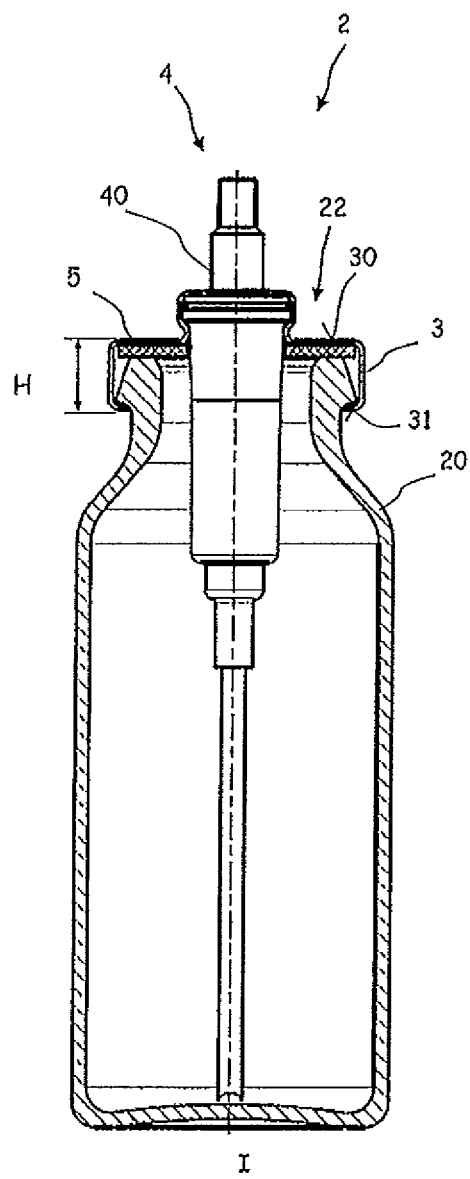
FIG. 2 shows schematically a container 2 for a dispenser.

The container 2 which is illustrated in FIG. 2 comprises a main body 20 for storing a medium, with an opening 22 which is closed by a crimped sleeve 3. A pump unit 4 is supported by means of the crimped sleeve 3. The pump unit 4 comprises a piston 40 which is displaceable in an actuating direction I counter to the force of a restoring spring (not visible) in order to discharge the stored medium. The piston 40 illustrated protrudes from the main body 20. The design of the pump unit 4 is merely by way of example.

A sealing element 5 is arranged between the main body 20 and the crimped sleeve 3. The container 2 forms a prefitted constructional unit. A suitable dispenser head 1 is fittable on the container 2, more precisely on the crimped sleeve 3 of the container 2. For this purpose, the crimped sleeve 3 has two substantially planar supporting surfaces 30, 31 arranged perpendicularly to the actuating direction I.

For the assembly of the dispenser head 1, which is illustrated in FIG. 1, on the container 2 according to FIG. 2, the dispenser head 1 comprises an intermediate element 10 with a receiving opening 11 for the container 2.

In the exemplary embodiment illustrated, a latching geometry is provided on the receiving opening 11, said latching geometry permitting the dispenser head 1 to be snapped onto the crimped sleeve 3 of the container 2. In the exemplary embodiment illustrated, the latching geometry comprises more than one, in particular four, latching hooks 12 or latching projections, wherein only two latching hooks 12 are visible in FIG. 1. The latching hooks 12 each have a shaped slope 120, the shaped slopes permitting or at least facilitating an introduction of the container 2 along the actuation direction I into the intermediate element 10. In one refinement, latching projections are provided, the latching projections having hook stops which are substantially perpendicular to the actuating direction I. In the exemplary embodiment illustrated, the latching hooks 12 are designed as spring arms which engage around the inserted crimped sleeve 3 and, after latching, prevent a relative movement of the container 2 and the intermediate element 10 for removing the container 2 from the intermediate element 10. The latching hooks 12 are suitably dimensioned for secure latching.

The intermediate element 10 is furthermore provided with stops 13 which project into the interior of the intermediate element 10, likewise interact with the crimped sleeve 3 and limit an insertion movement of the container 2 into the intermediate element 10. After the container 2 has been inserted into the intermediate element 10, the crimped sleeve 3 is therefore arranged between the latching hooks 12 and the stops 13 of the intermediate element 10 and is thus connected to the intermediate element 10. In the exemplary embodiments illustrated, a distance between the latching hooks 12 and the stops 13 is greater than a height H of the crimped sleeve 3, and therefore the crimped sleeve 3 is latched to the intermediate element 10 with play.

The dispenser head 1 illustrated in FIG. 1 furthermore comprises an actuating handle 14 which is coupled to the intermediate element 10 and, in the exemplary embodiment illustrated, is designed as a housing of the dispenser head 1.

An applicator tip 15 with a discharge opening 16 for the medium is provided on the actuating handle 14 opposite the receiving opening 11 for the container 2 according to FIG. 2. The discharge opening 16 is connectable via a discharge channel 17 to an outlet of the pump unit 4 arranged in the container 2. The applicator tip 15 is suitably designed for use, for example in the form of a nosepiece. The discharge opening 16 is closable as required by means of a cap (not illustrated). A pin 7 by which the pump unit 4 is actuable is provided in the discharge channel 17.

The actuating handle 14 is displaceable relative to the intermediate element 10 in the actuating direction I for a discharge. A displacement here takes place along a displacement distance limited by stops. The reversing points of the displacement distance are referred to as upper and lower dead centre, wherein, when the upper dead centre is reached, the actuating handle 14 and the intermediate element 10 are pushed apart to the maximum extent and, when the lower dead centre is reached, the components are pushed one inside the other to the maximum extent.

In order to prevent an undefined position of the actuating handle 14 relative to the intermediate element 10 during assembly of the dispenser head 1 to the container 2, connecting elements are provided, said connecting elements bringing about a retaining force between the intermediate element 10 and the actuating handle 14, the retaining force being opposed to a relative movement between the intermediate element 10 and the actuating handle 14 in the actuating direction I.

In the exemplary embodiment illustrated, the intermediate element 10 has, on an edge opposite the receiving opening 11, a peripheral, radially outwardly projecting latching hook 100 which serves as a connecting element. The latching hook 100 engages in a groove which is formed on the actuating handle 14 by a radially inwardly projecting latching hook 141 and more than one, preferably four, projections 142 which are distributed over the circumference and project into the interior of the actuating handle 14.

In other refinements, a plurality of latching hooks which are distributed in the circumferential direction are provided on the intermediate element 10 and/or the actuating handle 14. A latching-hook size and/or a distance between the latching hooks is preferably selected here in such a manner that release of the connection by rotation is not possible. In other refinements, at least the latching hooks of the intermediate element 10 and the projections 142 are dimensioned in such a manner that the connection is releasable by rotation. Alternatively, in other refinements, apertures are provided on a circumferential surface of the actuating handle 14, with corresponding latching hooks which are distributed over the circumference engaging in said apertures.

The latching hooks 100, 141 and the projections 142 have mutually facing boundary surfaces by means of which they bear against each other in the state illustrated in FIG. 1, and therefore a retaining force is transmitted via the boundary surfaces. The intermediate element 10 and/or the actuating handle 14 are formed from an elastic material, and therefore, by application of an assembly force in the actuating direction I that exceeds the retaining force, the latching hook 100 moves over the projections 142 and therefore an axially fixed connection between the intermediate element 10 and the actuating handle 14 is released. For this purpose, the latching hook 100 has a shaped slope on a side facing the projection 142. On that side of the latching hook 100 which faces the latching projection 141, stop surfaces arranged substantially perpendicularly to the actuating direction I prevent the projections 142 from being moved over again by the latching hook 100 when a force is applied in the opposite direction.

After assembly, the projections 142 and the latching hooks 100 also serve to limit the displacement distance during a discharge. By means of the connecting elements, the actuating handle 14 is therefore fixed to the intermediate element 10 in a region behind the upper dead centre, and therefore, during the assembly, the components are pushed apart over the region of the displacement distance.

FIGS. 3 to 5 show an assembly of the dispenser head according to FIG. 1 on a container 2 according to FIG. 2.

As can be seen in FIG. 3, the dispenser head 1 and the container 2 are provided as preassembled constructional units. In particular, it is provided, for example, that a crimped sleeve 3 closing the main body 20 of the container 2 with a pump unit 4 held by said crimped sleeve is attached after the container 2 has been filled.

The dispenser head 1 and the container 2 are oriented coaxially to each other and are moved towards each other on the actuating handle 14 by application of an assembly force F acting in the actuating direction I. In the first assembly step illustrated in FIG. 3, the actuating handle 14 is fixed on the intermediate element 10 by means of the connecting elements 100, 141, 142. A force engagement point of the assembly force F is illustrated merely by way of example and is suitably selectable by a person skilled in the art. For example, in one refinement, an assembly force for fastening the dispenser head 1 to the container 2 is applied to the intermediate element 10.

During a movement of the dispenser head 1 relative to the container 2, the intermediate element 10 is latched to the container 2, more precisely to the crimped sleeve 3, as illustrated schematically in FIG. 4. In the exemplary embodiment illustrated, the latching hooks 12 of the latching geometry are designed as spring arms, wherein a force by means of which the latching hooks 12 are elastically deformed is applied to the shaped slopes 120 by the inserted crimped sleeve 3. The shaped slopes 120 on the latching hooks 12 also bring about a centring of the dispenser head 1 relative to the container 2. When the force on the shaped slopes 120 ceases, the latching hooks 12 spring back into the original shape behind the inserted crimped sleeve 3. After latching, the latching hooks 12 interacting with the crimped sleeve 3 prevent a relative movement of the container 2 and of the intermediate element 10 for removing the container 2 out of the intermediate element 10. The latching geometry comprising the latching hooks 12 for fastening the intermediate element 10 to the crimped sleeve 3, and the connecting elements 100, 141, 142 are coordinated with each other here in such a manner that a retaining force applied by the connecting elements 100, 141, 142 is greater than a force to be applied for the latching. When the assembly force F is applied, a snapping of the intermediate element 10 onto the crimped sleeve 3 therefore occurs first.

A movement of the intermediate element 10 relative to the crimped sleeve 3 on account of the acting assembly force F is limited by the stops 13—as illustrated in FIG. 5. The stops 13 therefore stop a movement of the intermediate element 10 owing to the applied assembly force F. By application of a further assembly force acting in the actuating direction I, forces which exceed the retaining force of the connecting elements 100, 141, 142 then act on the connecting elements 100, 141, 142. As illustrated in FIG. 5, this results in a connection between the intermediate element 10 and the actuating handle 14 being released and the latching hook 100 moving over the projections 141.

FIGS. 6 and 7 show schematically an actuation of the fitted dispenser head 1 according to FIG. 1 for dispensing a medium. As illustrated in FIG. 6, for an actuation a force has to be applied to the actuating handle 14 in the actuating direction 1, said force being used to displace the actuating handle 14 with the pin 7 relative to the container 2. Owing to the movement, the piston 40 is displaced counter to the force of the restoring spring by means of the pin 7. In the exemplary embodiment illustrated, a displacement distance of the actuating handle 14 is limited by an adjustment distance of the piston 40. In the state illustrated, the latching hooks 100 therefore do not strike against a boundary surface of the actuating handle 14, which boundary surface faces away from the container 2, but rather are spaced apart from said boundary surface, as illustrated.

When the actuating force B ceases, the actuating handle 14 and the intermediate element 10 are pushed apart by the force of the restoring spring of the pump unit 4. A displacement distance is limited here by the connecting elements 100, 142, wherein the latching hook 100 strikes against a side of the projections 142, which side faces away from the latching hook 142 at the edge of the actuating handle 14, and, owing to the design of the latching hook 100 of the intermediate element 10 and of the projections 142, the latching hook 100 is prevented from moving over the projections 142.

The invention claimed is:

1. A dispenser head for dispensing a liquid or pasty medium, the dispenser head being fastenable to a container storing the medium, the dispenser head comprising an intermediate element with a receiving opening for receiving the container and an actuating handle for actuating a discharge of the medium coupled displaceably in an actuating direction to the intermediate element, wherein at least one of the intermediate element and the actuating handle has at least one releasable connecting element providing a retaining force between the intermediate element and the actuating handle, the retaining force being opposed to a relative movement between the intermediate element and the actuating handle in the actuating direction, and wherein the receiving opening has a latching geometry for fastening to the container, wherein the latching geometry is designed in such a manner that the intermediate element is snappable or pushable onto the container by a movement in the actuating direction, and a connection force applied to the actuating handle for snapping or pushing the intermediate element onto the container is smaller than the retaining force applied by the at least one connecting element between the intermediate element and the actuating handle in the actuating direction.

2. The dispenser head according to claim 1, wherein, after release of the at least one connecting element, the intermediate element and the actuating handle are coupled displaceably to each other within a displacement distance in the actuating direction, and the at least one connecting element is arranged outside the displacement distance.

3. The dispenser head according to claim 1, wherein at least one stop is provided on the receiving opening, said stop being used to limit a movement of the intermediate element relative to the container in the actuating direction during engagement of the intermediate element with the container.

4. A dispenser for a liquid or pasty medium, with a container storing the medium and with a dispenser head fastened to the container, the dispenser head including an intermediate element with a receiving opening receiving the container and an actuating handle for actuating a discharge of the medium coupled displaceably in an actuating direction to the intermediate element, wherein at least one of the intermediate element and the actuating handle has at least one releasable connecting element providing a retaining force between the intermediate element and the actuating handle, the retaining force being opposed to a relative movement between the intermediate element and the actuating handle in the actuating direction, and wherein the receiving opening has a latching geometry for fastening to the container, wherein the latching geometry is designed in such a manner that the intermediate element is snappable or pushable onto the container by a movement in the actuating direction, and a connection force applied to the actuating handle for snapping or pushing the intermediate element onto the container is smaller than the retaining force applied by the at least one connecting element between the intermediate element and the actuating handle in the actuating direction.

5. The dispenser according to claim 4, wherein a crimped sleeve is arranged on an opening of the container.

6. A method for fastening a dispenser head, for dispensing a liquid or pasty medium, to a container storing the medium, wherein the dispenser head comprises an intermediate element with a receiving opening for receiving the container and an actuating handle for actuating a discharge of the medium coupled displaceably in an actuating direction to the intermediate element, wherein, during fastening of the intermediate element to the container by applying a connection force to the actuating handle, a relative movement between the intermediate element and the actuating handle in the actuating direction is blocked by at least one connecting element providing a retaining force in the actuating direction, and, after the intermediate element is fastened to the container, the at least one connecting element is released to allow for movement of the actuating handle relative to the intermediate element.

7. The method according to claim 6, wherein the receiving opening has a latching geometry for the fastening to the container, wherein the intermediate element is snapped or pushed onto the container by movement of the actuating handle in the actuating direction before an exceeding force acts on the at least one connecting element, said exceeding force exceeding the retaining force applied by the at least one connecting element between the intermediate element and the actuating handle in the actuating direction.

8. The method according to claim 7, wherein a movement of the intermediate element relative to the container during engagement of the intermediate element with the container is limited by at least one stop arranged on the receiving opening, wherein, by a further movement of the actuating handle in the actuating direction, the exceeding force exceeding the retaining force is applied to the at least one connecting element in the actuating direction to release the at least one connecting element.

9. The method according to claim 6, wherein at least one of a valve unit and a pump unit is prefitted on an opening of the container by a crimped sleeve.

\* \* \* \* \*